(12) United States Patent
Yang et al.

(10) Patent No.: US 11,458,080 B2
(45) Date of Patent: Oct. 4, 2022

(54) COMPOSITIONS COMPRISING SPECIFIC SURFACTANTS AND HIGH LEVELS OF GLYCERIN

(71) Applicant: Conopco, Inc., Englewood Cliffs, NJ (US)

(72) Inventors: Lin Yang, Woodbridge, CT (US); Prem Chandar, Shelton, CT (US); Jing Hu, Trumbull, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/334,954

(22) PCT Filed: Sep. 13, 2017

(86) PCT No.: PCT/EP2017/073038
§ 371 (c)(1),
(2) Date: Mar. 20, 2019

(87) PCT Pub. No.: WO2018/054743
PCT Pub. Date: Mar. 29, 2018

(65) Prior Publication Data
US 2020/0022891 A1    Jan. 23, 2020

(30) Foreign Application Priority Data
Sep. 22, 2016 (EP) .................................. 16190191

(51) Int. Cl.
| | | |
|---|---|---|
| *A61K 8/34* | (2006.01) | |
| *A61K 8/44* | (2006.01) | |
| *A61K 8/46* | (2006.01) | |
| *A61Q 5/00* | (2006.01) | |
| *A61Q 19/00* | (2006.01) | |

(52) U.S. Cl.
CPC ............... *A61K 8/345* (2013.01); *A61K 8/44* (2013.01); *A61K 8/442* (2013.01); *A61K 8/463* (2013.01); *A61Q 5/00* (2013.01); *A61Q 19/00* (2013.01); *A61K 2800/596* (2013.01)

(58) Field of Classification Search
CPC ........ A61K 8/345; A61K 8/463; A61K 8/442; A61K 8/44; A61K 2800/596; A61K 8/466; A61Q 19/00; A61Q 5/00; A61Q 19/10
See application file for complete search history.

(56) References Cited

U.S. PATENT DOCUMENTS

| | | | |
|---|---|---|---|
| 4,728,457 A | 3/1988 | Fieler et al. | |
| 4,788,006 A | 11/1988 | Bolich, Jr. et al. | |
| 5,716,919 A | 10/1998 | Sano | |
| 5,948,739 A | 9/1999 | Inman | |
| 6,001,344 A | 12/1999 | Villa | |
| 6,303,108 B1 | 10/2001 | Roulier et al. | |
| 6,387,857 B2 | 5/2002 | Chambers et al. | |
| 7,879,780 B2 | 2/2011 | Tsaur | |
| 7,910,090 B2 * | 3/2011 | Dueva-Koganov | ...... A61K 8/20 424/401 |
| 2001/0001783 A1 | 5/2001 | Nystrand et al. | |
| 2003/0108576 A1 | 6/2003 | Bielli | |
| 2006/0183662 A1 | 8/2006 | Crotty et al. | |
| 2010/0075881 A1 | 3/2010 | Tsaur | |
| 2011/0245124 A1 | 10/2011 | Tsaur et al. | |
| 2018/0221259 A1 | 8/2018 | Potanin et al. | |
| 2019/0388314 A1 | 12/2019 | Tsaur et al. | |

FOREIGN PATENT DOCUMENTS

| | | |
|---|---|---|
| CN | 1339961 | 3/2002 |
| CN | 101160154 | 4/2008 |
| CN | 101862275 | 10/2010 |
| CN | 102078280 | 6/2011 |
| CN | 103356408 | 10/2013 |
| CN | 104257521 | 1/2015 |
| CN | 104971011 | 10/2015 |
| CN | 105078776 | 11/2015 |
| EP | 0194097 | 9/1986 |
| EP | 0559375 | 9/1993 |
| EP | 1000606 | 5/2000 |
| EP | 1029532 | 8/2000 |
| EP | 1237534 | 1/2005 |
| JP | H10219289 | 8/1998 |
| JP | 2002037726 | 2/2002 |
| JP | 2007055925 | 3/2007 |
| WO | WO9401084 | 1/1994 |
| WO | WO0142409 | 6/2001 |
| WO | WO2004009039 | 1/2004 |
| WO | WO2011120780 | 10/2011 |
| WO | WO2013175221 | 11/2013 |
| WO | WO2017182264 | 10/2017 |

OTHER PUBLICATIONS

CN104800091A Machine Translation (Year: 2015).*
KELTROL/KELZAN; Xanthan Gum Book; CPKelco; 2007; pp. 1-21; XP002769065.
Search Report and Written Opinion in EP17155142; dated May 23, 2017.
Search Report and Written Opinion in PCTEP2018050207; dated Mar. 2, 2018.
IPRP1 in PCTEP2018050207; dated Aug. 13, 2019.
IPRP2 in PCTEP2017073038; dated Feb. 26, 2019.
Co-pending Application, U.S. Appl. No. 16/480,764.
Search Report and Written Opinion in EP16190191; dated Nov. 23, 2016.
Search Report and Written Opinion in PCTEP2017073038; dated Dec. 11, 2017.
Written Opinion 2 in PCTEP2017073038; dated Aug. 14, 2018.
Written Opinion 3 in PCTEP2017073038; dated Jan. 3, 2019.
Huang, X. et al.; Hydrocolloids in emulsions: particle size distribution and interfacial activity; Food Hydrocolloids; 2001; pp. 533-542; vol. 15; Elsevier.
Opposition Notice in EP17764417 (EP3515400); dated Nov. 17, 2021; European Patent Office (EPO); with English Translation.

* cited by examiner

*Primary Examiner* — Quanglong N Truong
(74) *Attorney, Agent, or Firm* — Krista A. Kostiew

(57) ABSTRACT

The present invention relates to personal care cleansing compositions prising specific surfactant systems used in combination with high levels of glycerin.

20 Claims, No Drawings

COMPOSITIONS COMPRISING SPECIFIC SURFACTANTS AND HIGH LEVELS OF GLYCERIN

CROSS REFERENCE TO RELATED APPLICATIONS

The present application is a U.S. National Phase Application under 35 U.S.C. § 371 of International Application No. PCT/EP2017/073038, filed on Sep. 13, 2017, which claims priority to European patent application No. 16190191.3 filed on Sep. 22, 2016, the contents of which are incorporated herein in their entireties.

FIELD OF THE INVENTION

The present invention relates to personal care cleansing compositions comprising cleansing surfactant, preferably mild cleansing surfactant and high levels (e.g., 40% to 80% by wt. or 50% to 80% by wt.) of glycerin. More particularly, it has been found that, when combined with specific types of mild surfactants, high glycerin compositions provide even greater mildness (as measured for example by transepidermal water loss, or "TEWL" test, or by Skicon test) and superior deposition of the glycerin relative to surfactants typically used in such personal care (e.g., aqueous personal wash cleansing) compositions.

BACKGROUND OF THE INVENTION

Personal care compositions (which generally refer to rinse-off or leave-on compositions suitable for application on mammalian, keratinous tissue) have been employed to cleanse and moisturize skin and/or hair, deliver actives, hide imperfections and to reduce oiliness/shine associated with sebum.

Consumers typically will prefer compositions which are mild to the skin and/or deliver moisturizing feel or other consumer benefits. Mildness, in turn, can be associated, for example, with lower levels of skin irritation, and lesser levels of water loss (as measured, for example, by Skicon and/or TEWL test noted above).

One way of meeting these needs is by enhancement of glycerin deposition (which provide greater moisturizing feel).

Quite unexpectedly, applicants have now found that, through the use of specific surfactants which are N-acyl derivatives of mono- and/or dicarboxylic acids, in combination with high glycerin containing compositions, they have been able to not only take advantage of the mild nature of the surfactants, but have further found that these surfactants provide enhanced glycerin deposition relative to the use of other types of surfactants in the same high glycerin systems. Preferably, the mild surfactants comprise 50% or more of the surfactant system. Preferably the level of certain amphoteric surfactants, especially betaines, are minimized (less than 40%, preferably less than 30% of surfactant system); preferably both mild surfactants are 50% or more of surfactant system; and level of amphoteric, especially betaine, is less than 40%.

Applicants have previously filed applications relating to the use of N-acyl derivatives in personal care compositions, for example, EP Application No. 16166487. EP Application No. 16166487 is concerned with the provision of benefit agents such as triglycerides and petrolatum from nanoemulsions in small droplet size and does not relate to high glycerin compositions or means of enhancing glycerin deposition.

High glycerin compositions are also known. Applicants are aware of no reference, however, which discloses the specific combination of N-acyl derivatives of amino acid and high levels of glycerin; or recognizes that such surfactants provide enhanced moisturization and/or enhanced glycerin deposition relative to other surfactants.

BRIEF DESCRIPTION OF THE INVENTION

The present invention provides personal care cleansing compositions, preferably, personal wash cleansing compositions (preferably, rinse-off composition) comprising:
1) 40 to 90%, preferably 50 to 90%, more preferably 55 to 90% or 60 to 80% glycerin;
2) 3 to 25% of a surfactant selected from the group consisting of salts of N-acyl derivatives of dicarboxylic amino acid (e.g., aspartic acid, glutamic acid), salts of N-acyl derivatives of monocarboxylic acids (glycine, alanine) and mixtures of such derivatives of mono- and dicarboxylic acids; and
3) 5 to 55% water.

Preferred surfactants include glutamates.

Although other surfactants may be present, the noted surfactants should preferably comprise the majority of the surfactant system, e.g., 50 to 100% of the surfactant system, or 60 to 90%, or 70 to 90% of the surfactant system.

As indicated, the composition may further comprise 0 to 15% by wt., preferably 1 to 10% by wt. of a co-surfactant selected from the group consisting of nonionic surfactant; amphoteric and/or zwitterionic surfactant; cationic surfactants; and mixtures thereof. Preferably, the derivatives of mono- and dicarboxylic acid is present at a level of 50% to 100%, sometimes 60% to 90% of the surfactant system. Preferably, the derivative is at least 50.1, preferably at least 50.5% of the composition (e.g., 50.5 to 90%).

Applicants have also found that certain specific betaine surfactants (e.g., cocoamido propylbetaine) seem to have a detrimental effect on deposition when used at higher levels. This is not readily understood since other co-surfactants, such as amphoacetates have no such negative effects, even at higher level. Thus, alkyl amido betaine, if used, should preferably be used at levels less than 50%, more preferably less than 40%, even more preferably less than 30%, more preferably less than 25% and even more preferably, less than 20% of the surfactant system.

Applicants have also found that, within a defined high glycerin range (e.g., 40% to 90%), the claimed amino acid containing surfactant systems (e.g., glutamate) drive greater delivery of glycerin compared to delivery from other surfactant systems (e.g., those comprising sodium lauryl ether sulfate or non-amino acid surfactants such as glucosamides).

In another form, the compositions may comprise:
1) 40 to 90%, preferably 50 to 90%, more preferably 55 to 90% or 60 to 80% glycerin;
2) 3 to 25% of a surfactant which is a salt of N-acyl derivatives of taurine (sulfate group instead of carboxylic group), and
3) 15 to 55% water.

The salts of derivatives of taurine may also be used in combination with the salts of N-acyl derivatives of mono- and di-carboxylic acids. The percent of surfactant of any such mixture is also 3 to 25% by wt. of the total composition.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The present invention provides personal care compositions, preferably rinse-off personal care compositions, comprising high levels of glycerin and specific surfactant actives. Unexpectedly, applicants have found that the specific surfactants systems (comprising N-acyl derivatives of amino acid, preferably present in an amount at least 50% to 100% or 60 to 90% of the surfactant system) drive glycerin deposition higher than when compared to the delivery of glycerin from other surfactant systems.

Specifically, compositions of the invention comprise
(1) 40 to 90% or 50 to 90% or 55 to 90% or 60 to 80% by wt. of total composition glycerin;
(2) a surfactant system comprising
   (a) 3 to 25% by wt. of total composition of a surfactant selected from the group consisting of salts of N-acyl derivatives of dicarboxylic amino acid (e.g., aspartic acid, glutamic acid), salts of N-acyl derivatives of monocarboxylic acids (glycine, alanine) and mixtures of such derivatives of mono- and dicarboxylic acids; and
   (b) 0 to 15%, preferably 1 to 10% by wt. of total composition, of a co-surfactant selected from the group consisting of nonionic surfactant; amphoteric and/or zwitterionic surfactant; cationic surfactant and mixtures thereof. Preferably, the derivatives of mono- and dicarboxylic acid is present at a level of 50% to 100%, especially 50% to 90% of the surfactant system. Preferably, the derivative is at least 50.1, preferably at least 50.5% of the composition; and
(3) 5 to 55% water.

As noted, a separate form may comprise (a) salts of N-acyl derivatives of taurine (e.g., taurate). Further, compositions may comprise 3 to 25% of mixtures of the salts of carboxylic acid and salts of taurine derivatives.

The invention further relates to a method of enhancing glycerin deposition by applying compositions noted above to the hair or body (e.g., to the skin)

Compositions of the invention comprise, as noted, 40 to 90% glycerin. While glycerin is preferred polyol, other polyol may be used. These include sorbitol, propylene glycol, polypropylene glycol and mixtures thereof (including preferably, mixtures of one of these with glycerin).

The polyols (e.g., glycerin) have quite unexpectedly been found to deposit better from the specific surfactant systems of the invention compared to deposition of polyol from other surfactant or surfactant systems (e.g., typical anionics such as alkyl sulfates).

The lower level of polyol used may be 40 or 45 or 50% (and all digits between) and is preferably 51% and higher, including 51 to 65 and all digits between. The upper range may be 65 to 90 and all digits in between. Of course, any digit between 41 and 89 can theoretically be upper or lower limit. For example, 89% can be the lower limit and 90% can be the upper limit. Preferred ranges are 50 to 90% or 55 to 90% or 60 to 80%.

The compositions of the invention further comprise a surfactant selected from the group consisting of salts of N-acyl derivatives of dicarboxylic amino acid (e.g., aspartic acid, glutamic acid), salts of N-acyl derivatives of monocarboxylic acids (e.g., glycine, alanine, sarcosine) and mixtures of such derivatives of mono- and dicarboxylic acids; and 5 to 55% water.

Preferred di-carboxylic amino acid emulsifiers are acylglutamate and acylaspartate surfactants. Preferred monocarboxylic amino acid emulsifiers are acylglycinate, acylalanate, and acyl sarcosinate. Preferably, these are potassium and/or sodium salts of N-acyl derivatives of amino acids.

There are typically two formats of amino acid surfactants commercially available. One is powder or flake format, which is typically more expensive and high in purity. Examples of solid dicarboxylic amino acid surfactants include:
   sodium N-cocoyl-L-glutamate (e.g., Amisoft® CS-11 by Ajinomoto)
   sodium N-lauroyl-L-glutamate (e.g., Amisoft® LS-11 by Ajinomoto)
   sodium N-myristoyl-L-glutamate (Amisoft® MS-11 by Ajinomoto)
   potassium N-cocoyl_I-Glutamate (e.g., Amisoft® CK-11 by Ajinomoto)
   potassium N-myristoyl-L-glutamate (Amisoft® MK-11 by Ajinomoto)
   potassium N-lauroyl-L-glutamate (Amisoft® LK-11 by Ajinomoto)
   Sodium Lauroyl Aspartate (AminoFoamer™ FLMS-P1 by Asahi Kasei Chemical Corporation)
   Sodium Lauroyl Glutamate (Aminosurfact™ ALMS-P1/S1 by Asahi Kasei Chemical Corporation)
   Sodium Myristoyl Glutamate (Aminosurfact™ AMMS-P1/S1 by Asahi Kasei Chemical Corporation)

Examples of solid monocarboxylic amino acids surfactants include:
   a sodium cocoyl glycinate (e.g., Amilite® GCS-11 by Ajinomoto)
   a potassium cocoyl glycinate (e.g., Amilite® GCK-11 by Ajinomoto The amino acid surfactants typically comprise 3 to 25% by wt. of total composition. The lower limit can be 3 or 4 or 5 or 6 or 7 through 15%. The upper limit can be 15 to 25% and all digits in between. Of course, any number from 4 to 24 can be upper or lower limit. A preferred level is 5 to 15% or 7 to 12% by wt.

Compositions of the invention comprise 5 to 55% water.

In addition, compositions of the invention may comprise 0 to 10% of a benefit agent. One class of ingredients is nutrients used to moisturize and strengthen, for example, the skin. These include:
   a) vitamins such as vitamin A and E, and vitamin alkyl esters such as vitamin C alkyl esters;
   b) lipids such as cholesterol, cholesterol esters, lanolin, creaminess, sucrose esters, and pseudo-ceramides;

c) liposome forming materials such as phospholipids and suitable amphophilic molecules having two long hydrocarbon chains;
d) essential fatty acids, poly unsaturated fatty acids, and sources of these materials;
e) triglycerides of unsaturated fatty acids such as sunflower oil, primrose oil avocado oil, almond oil;
f) vegetable butters formed from mixtures of saturated and unsaturated fatty acids such as Shea butter;
g) minerals such as sources of zinc, magnesium, and iron.

As noted above, the majority of the surfactant system are the amino-acid derived surfactants noted. In addition, there may be present up to 50%, preferably 0-40% of a co-surfactant. Other anionic surfactants may be used (preferably at level of 0-40% of surfactant system) and these may include acyl isethionates and alkyl phosphates. It is preferred the co-surfactant be nonionic, amphoteric, zwitterionic, or cationic and may include ethoxylated alkyl sulfates, alkyl polyglucosides, alkyl amine oxides, betaines, amphoacetates sultaines, sulfosuccinates, lactylates and mixtures thereof. Applicants have noted that betaines (e.g., cocoamidopropyl betaine) appear to diminish deposition of glycerin from the system. As such, preferably, if betaine is used, it should comprise less than 50%, preferably less than 40%, more preferably less than 30% of the surfactant system.

In general, and without wishing to be bound by theory, applicants believe that surfactants which precipitate (e.g., glutamate) more quickly or easily from water phase tend to be effective to deposit the polyol (e.g., glycerin). The claimed amino acid and taurate surfactants are more like this than sodium lauryl ether sulfate, for example. Perhaps it is for this reason that high levels of glycerin (more surfactant available to interact with higher levels of glycerin) tend to be more effective with surfactants of the invention at glycerin deposition.

A second type of skin benefit agent is a skin conditioner used to provide a moisturized feel to the skin. Suitable skin conditioners include:
a) silicone oils, gums and modifications thereof such as linear and cyclic polydimethylsiloxanes, amino, alkyl, and alklyl aryl silicone oils;
b) hydrocarbons such as liquid paraffins, petrolatum, Vaseline, microcrystalline wax, ceresin, squalene, pristan, paraffin wax and mineral oil;
c) conditioning proteins such as milk proteins, silk proteins and glutens; d) cationic polymers as conditioners which may be used include Quatrisoft LM-200, Polyquaternium-24, Merquat Plus 3330-Polyquaternium 30; and Jaguar® type conditioners;
e) emollients such as esters of long chain fatty acids, such as isopropyl palmiate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:
a) antimicrobials such as 2-hydrozy-4,2',4'-trichlorodiphenylether (DP300) 2,6-dimethyl-4-hydroxychorobenzene (PCMX), 3,4,4'-trichlorocarbanilide (TCC), 3-trifluromethyl-4,4'-trichloromethyl-4,4'-dichlorocarbanilide (TFC), benzoyl peroxide, zinc salts, tea tree oil,
b) anti-acne agents such as salicylic acid, lactic acid, glycolic acid, and citric acid, and benzoyl peroxide (also an antimicrobial agent),
c) oil control agents including sebum suppressants, modifiers such as silica, titanium dioxide, oil absorbers such as micro sponges,
d) astringents including tannins, zinc and aluminum slats, plant extracts such as from green tea and Witch-hazel (Hammailes),
e) scrub and exfoliating particles, such as polyethylene spheres, agglomerated silica, sugar, ground pits, seeds, and husks such as from walnuts, peach, avocado, and oats, salts,
f) cooling agents such as methanol and its various derivatives and lower alcohols,
g) fruit and herbal extracts,
h) skin calming agent such as aloe vera,
i) essential oils such as mentah, jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geraniol, evening primrose, camphor, tymol, spirantol, penene, limonene and terpenoid oils.

Other benefit agents that can be employed include antiaging compounds, sunscreens, and in lightening agents.

In some embodiments, the benefit agent is a polar benefit agent. Preferred polar benefit agents include ethyl resorcinol (ER) and water-soluble vitamins. Preferred non-polar benefit agents, e.g., hexyl resorcinol, may also be used.

As indicated in addition to novel compositions of the invention, the invention further comprises a method of enhancing glycerin deposition using the compositions of the invention, e.g., applying composition of the invention to hair or skin.

EXAMPLES AND PROTOCOL

Experiment procedures for measuring glycerin delivery from a cleanser:

Glycerin Extraction from Skin
a. Pig skin which has been stored at anywhere from −80° C. to room temperature is removed from storage on the day of the experiment and is left standing until it has thawed out. The pig skin is removed from storage on a cutting board and cut into 4×4 cm pieces. The 4×4 cm pig skin pieces are then loosely wrapped by saline-soaked gauze prior to product application.
b. The 4×4 cm skin pieces are pre-rinsed with 37° C. tap water for 15 seconds. The flow rate of water is 50 mL/minute.
c. A 2.5 cm ring is placed on the skin. 250 μL of a product is applied in the ring, and the skin is rubbed in circular motion with a volumetric stopper for 90 seconds.
d. The ring is replaced by a 3.0 cm ring. 5 mL of water is added in the ring and the skin is washed by rubbing in a circular motion for 15 seconds with the stopper. Using Q-tip, the shallow dent pressured edge of the ring on the skin is gently wiped to clean up the glycerin residue. The wash solution is discarded with a transfer pipet. Wash is repeated once.
e. The ring is removed from the skin. The skin is cut into 2×2 cm piece (the center of ring used to rub/rinse the skin) and the 2×2 cm piece skin is transferred into a 20-mL glass vial.
f. 10.0 mL of deionized (DI) water is added in a 20 mL glass vial for extraction by shaking the vial for 30 minutes, and this is followed by a 10 minute sonication.

g. The extraction solution is filtered with 0.45 μm PTFE (polytetrafluoroethylene) membrane filter. The filtered solution is collected for derivative reaction.
h. Blank skin is prepared by cutting 2×2 cm skin and gently washing the skin with 37° C. tap water for 15 seconds. The skin is transferred into 10.0 mL of water for extraction as deposition sample is prepared.
i. Triple preparations for all samples and blank skin are essential.

Preparation of Derivative Regents:
a. Reagent A, about 3 mM NaIO$_4$ in water: Weigh 6.5 mg of NaIO$_4$ to a vial, add 9 mL of DI water and 1 mL of acetic acid, dissolve and mix well, and then add 0.77 g of ammonium acetate and mix well.
b. Reagent B, about 100 mM C$_5$H$_8$O$_2$ in isopropyl alcohol: in 25 mL of volumetric flask, transfer 0.25 mL of C$_5$H$_8$O$_2$, fill the flask with isopropyl alcohol to the mark. Store this reagent in a dark and cool place.

Preparation of Glycerin Standards:
a. In a 100 mL of volumetric flask, weight 50 mg±5 mg of Glycerin, add DI water to dissolve and mix well. Bring to the mark with DI water. This is the glycerin standard stock solution.
b. Use above glycerin standard stock solution to prepare 4-5 concentrations of glycerin standard calibration solutions with glycerin concentration ranging from 10-200 μg/mL with DI water.

Glycerin Derivative Reaction:
a. DI water, glycerin standards with concentration ranging from 10-200 μg/mL, blank skin extraction and sample extraction are prepared for the reaction.
b. Transfer 400 μL of Reagent A in each vial, pipet 150 μL of water, or standards, or blank samples, or deposition samples, mix well and leave the reaction in room temperature for 30 minutes.
c. After 30 minutes into the reaction, transfer 1.0 mL of reagent B into the vials, mix well and leave the reaction in room temperature for another 30 minutes.
d. Place the vials in HPLC sampler tray for 15-20 minutes to cool down the sample solution to 4° C. prior to injecting.
e. Process the HPLC data and calculate the glycerin derivative delivery in μg/cm$^2$.

Calculation $Y = M*X + b$   Glycerin standard linearity:

Y: peak area of the glycerin derivative
X: concentration of glycerin in standard solution
M: slope of the standard linearity Glycerin Concentration (μg·cm$^{-2}$) = $(PA_{sp1} - B) * DF * V / M / 4$ μg·cm$^{-2}$: glycerin amount retained in deposition sample
$PA_{sp1}$: sample peak area
B: Y intercept
DF: dilution factor
V: volume in mL for sample extraction
M: Slope of standard linearity
4: area for a size 2×2 cm of skin Experiment procedures for measuring glycerin delivery from a cleanser in a clinical study:

Subjects are 18-65 years old male or females, having slightly dry skin on forearms (visual grade of 0.5-2 on a 0-6 dryness grading scale). Minimum 30 subjects are needed to complete the study. Subjects should have even dryness score on both arms (within a grade of 0.5). Six sites on forearms (3 sites on each arm) are tested. This clinical study is a randomized, evaluator-blind/subject-blind controlled normal wash study and with minimum 30 subjects is considered statistically significant.

Controlled washes were conducted twice daily on each site for 4 weeks (27 days), with 4 to 5 hours apart between the two washes in a day. A five day conditioning phase was done by washing with a commercial soap bar comprising sodium tallowate, sodium cocoate, cocamidopropyl betaine twice daily (−5 day starting). On Days 1, 7, 14, 21, and 28, morning visits before wash, the subjects were acclimated in an environmentally controlled room maintained at 66.6° F. to 71.9° F. and at 24% to 55% relative humidity for at least 30 minutes prior to instrumental assessments. One TEWL reading was collected from each site with either a DermaLab (Cortex Technology) or RG-1 (cyber DERM, Inc.) evaporimeter. Triplicate Skicon (200 EX with MT8C probe; I.B.S., Co., Ltd.) readings were taken from each site. Data presented is the mean change from baseline.

During the study period, subjects were asked to avoid using any skin care products on testing sites (forearms). They were required to take evening showers every day with a commercial soap bar comprising sodium lauroyl isethionate, stearic acid, sodium tallowate or sodium palmitate, lauric acid (e.g., Dove® bar from Unilever), but to avoid applying any cleansing product on arms (it is acceptable if residual solution flows down on treated site (e.g., forearm) when showering)

EXAMPLES

In order to demonstrate generally that surfactant systems comprising 40 to 90% glycerin provide enhanced skin properties, applicants measured properties of:
(a) surfactant systems (e.g., SLES and CAPB; glutamate and CAPB) containing no glycerin; and
(b) identical surfactant systems in 70% glycerin system.
Specifically, Examples 1-2 and Comparatives A and B below (a commercially available shows gel comprising sodium lauroyl ether sulfate and cocoamidopropyl betaine as 12% surfactant in an aqueous system without glycerin, i.e., Axe® from Unilever, was used as a control) used a Skicon test to determine skin hydration based on conductance measurements (enhanced hydration correlates with increased conductance).

TABLE 1

|  | Example 1 | Comparative A | Example 2 | Comparative B | Control |
|---|---|---|---|---|---|
| SLES (sodium lauryl ether surfactant) | 6.75% | 6.75% |  |  |  |
| CAPB (cocoamidipropyl betaine) | 2.75% | 2.75% | 2.75% | 2.75% |  |
| Water | To balance | To balance | To balance | To balance |  |
| Glutamate (Sodium lauroyl glutamate) |  |  | 6.75% | 6.75% |  |

TABLE 1-continued

|  | Example 1 | Comparative A | Example 2 | Comparative B | Control |
|---|---|---|---|---|---|
| Glycerin | 70% |  | 70% |  |  |
| Axe ® |  |  |  |  | 100% |

The conductance values, based on Skicon testing, are set forth in Table 2 below:

TABLE 2

|  | Conductance Values (measured in μ seconds) |
|---|---|
| Example 1 | 849 |
| Comparative A | 587 |
| Example 2 | 1274 |
| Comparative B | 605 |
| AXE | 68 |

As seen clearly from the examples in Table 1 and associated conductance values in Table 2, when the same surfactant system is used (e.g., SLES/CAPB or glutamate/CAPB) and the only difference is use of high glycerin as solvent (70/21 glycerin/water versus 100% water), conductance value (associated with enhanced hydration) of the system with high glycerin (Example 1 versus Comparative A; Examples 2 versus Comparative B) is far higher. The Skicon evaluation also demonstrates that, between a glutamate/CAPB system and a SLES/CAPB system (in high glycerin systems), glutamate systems provide superior hydration (e.g., Example 2 versus Example 1). In a commercially available shower gel (Axe®) comprising (total of about 12% surfactant) sodium laureth sulfate (SLS) and cocoamidopropyl betaine (CAPB) in a water system (no glycerin), conductance is much lower. Without wishing to be bound by theory, it is believed lower values in Axe® (less hydration) relative to Comparative A are because of greater amount of surfactant (less water). The direct comparison, however, as noted, is Comparative A versus Example 1.

Similarly, TEWL test was conducted to show skin barrier function during the clinical study (using the same examples as were used in Skicon test) and results were set forth in Table 3 below:

TABLE 3

|  | TEWL Values |
|---|---|
| Example 1 | 44.4 |
| Comparative A | 55.0 |

TABLE 3-continued

|  | TEWL Values |
|---|---|
| Example 2 | 26.1 |
| Comparative B | 37.8 |
| AXE | 81.6 |

TEWL: mean change from baseline. Flux density measured as $g/(m^2 \cdot h)$.

With transepidermal water loss test (TEWL), lower values are associated with superior skin barrier function. Thus, again it can be seen that high glycerin/water systems (Examples 1 and 2) had superior hydration compared to same surfactant systems using only water as solvent (Comparative A versus Example 1 and Comparative B versus Example 2). Further, again it can be seen that glutamate based surfactant system of Example 2 is superior to the SLES based surfactant system of Example 1. Also a water-based SLES and CAPB system again has inferior results than any of the glycerin system, and particularly relative to systems with predominantly amino acid based surfactant. Higher values of Comparative A versus Axe® are again believed associated with the fact that Axe® has more surfactant.

Example 3

In order to further demonstrate superiority of glutamate system versus SLES system, applicants again made compositions as set forth in Examples 1 and 2 above.

Using protocol noted above for measuring glycerin deposition, applicants measured glycerin delivery/deposition and obtained the following results.

TABLE 4

|  | Deposition (in $\mu g/cm^2$) |
|---|---|
| From composition of Example 1 (SLES) | 36.3 (±2.8) |
| From composition of Example 2 (glutamate) | 64.4 (±3.7) |

As clearly noted, glycerin delivery was far greater from amino acid based (e.g., glutamate based) system.

TABLE 5

Examples 3 to 5 and Comparatives C to F
Formulations that deliver more glycerin than other

|  | Ex 3 | Ex 4 | Ex 5 | Comparative C | Comparative D | Comparative E | Comparative F |
|---|---|---|---|---|---|---|---|
| Sodium lauroyl glutamate | 6.75 |  |  |  |  |  | 2.25 |
| Sodium laureth sulfate |  |  |  | 6.75 |  |  |  |
| Cocamidopropyl betaine | 2.25 |  |  | 2.25 |  |  | 6.75 |
| Sodium lauroyl sarcosinate |  | 9 |  |  |  |  |  |
| Sodium lauroyl glycinate |  |  | 9 |  |  |  |  |

TABLE 5-continued

Examples 3 to 5 and Comparatives C to F
Formulations that deliver more glycerin than other

|  | Ex 3 | Ex 4 | Ex 5 | Comparative C | Comparative D | Comparative E | Comparative F |
|---|---|---|---|---|---|---|---|
| Cocoyl methyl glucamide |  |  |  |  | 9 |  |  |
| Sodium dodecyl sulfate |  |  |  |  |  | 9 |  |
| Glycerin | 70 | 70 | 70 | 70 | 70 | 70 | 70 |
| Water | To 100% | To 100% | To 100% | To 100% | To 100% | To 100% | To 100% |
| pH | 6.5 (±0.2) | 6.5 (±0.2) | 6.5 (±0.2) | 6.5 (±0.2) | 6.5 (±0.2) | 6.5 (±0.2) | 6.5 (±0.2) |
| Glycerin delivery, ug/cm^2 | 99.24 (±7.8) | 84.64 (±8.3) | 77.58 (±7.9) | 63.38 (±5.4) | 54.36 (±11.9) | 45.09 (±5.2) | 43.64 (±9.3) |

The following can be noted from Examples 3-5 and Comparatives C-F. Comparatives C and E are examples of surfactant system comprising sodium laureth sulfate and CAPB system (Comparative C); and sodium dodecyl sulfate system (Comparative E). These are two common anionic systems and it is seen glycerin deposition is 63.38 and 45.09 $\mu g/cm^2$, respectively. Relative to these numbers, it can be seen that the predominant amino acid surfactant systems of Examples 3, 4 and 5 (i.e., glutamate/betaine, sarcosinate; glycinate) all have superior deposition.

Comparative D shows that non amino acid based system (glucamide) has less deposition.

Comparative E shows that a system where amino acid based surfactant is less than 50% of system also has less deposition. It is also noted that CAPB, which applicants have found can diminish deposition if used at 50% or more, comprises 75% of the surfactant system.

Examples 6-9: Preferred Co-Surfactants—CAPB Versus Amphoacetate

In order to demonstrate which specific co-surfactant are better to use in combination with dicarboxylic acid surfactant, applicants prepared Tables 6, 7, 8 and 9 noted below (Examples 6A-6D; 7A-7C; 8A-8C; and 9A-9E).

TABLE 6

|  | Ex 6A | Ex 6B | Ex 6C | Ex 6D |
|---|---|---|---|---|
| Sodium lauroyl glutamate | 9 | 6.75 | 4.5 | 2.25 |
| Cocamidopropyl betaine | 0 | 2.25 | 4.5 | 6.75 |
| Glycerin | 70 | 70 | 70 | 70 |
| Water | To 100% | To 100% | To 100% | To 100% |
| pH | 6.5 | 6.5 | 6.5 | 6.5 |
| Glycerin delivery, ug/cm² | 97.5 (±20.3) | 53.7 (±7.8) | 44.6 (±4.3) | 28.5 (±0.9) |

TABLE 7

|  | Ex 7A | Ex 7B | Ex 7C |
|---|---|---|---|
| Sodium laureth sulfate | 9 | 6.75 | 4.5 |
| Cocamidopropyl betaine | 0 | 2.25 | 4.5 |
| Glycerin | 70 | 70 | 70 |
| Water | To 100% | To 100% | To 100% |
| pH | 6.5 | 6.5 | 6.5 |
| Glycerin delivery, ug/cm² | 124.0 (±2.7) | 93 (±9.1) | 41 (±2.6) |

TABLE 8

|  | Ex 8A | Ex 8B | Ex 8C |
|---|---|---|---|
| Sodium lauroyl glycinate | 9 | 6.75 | 4.5 |
| Cocamidopropyl betaine | 0 | 2.25 | 4.5 |
| Glycerin | 70 | 70 | 70 |
| Water | To 100% | To 100% | To 100% |
| pH | 6.5 | 6.5 | 6.5 |
| Glycerin delivery, ug/cm² | 53.7 (±7.8) | 44.6 (±4.3) | 28.5 (±0.9) |

TABLE 9

|  | Ex 9A | Ex 9B | Ex 9C | Ex 9D | Ex 9F |
|---|---|---|---|---|---|
| Sodium lauroyl glutamate | 9 | 6.75 | 4.5 | 2.25 | 0 |
| Sodium lauroamphoacetate | 0 | 2.25 | 4.5 | 6.75 | 9 |
| Glycerin | 70 | 70 | 70 | 70 | 70 |
| Water | To 100% | To 100% | To 100% | To 100% | To 100% |
| pH | 6.5 | 6.5 | 6.5 | 6.5 | 6.5 |
| Glycerin delivery, ug/cm² | 124 (±14.1) | 106.0 (±4.8) | 116 (±16.7) | 102 (±9.8) | 94 (±10.4) |

As seen from the Tables, when CAPB specifically is combined with amino acid surfactants of the invention, glycerin delivery was affected much more strongly compared to use of same amino acids surfactants in combination with different co-surfactant.

First, it is noted that the data within each Table was done from the same pigskin, but pigskin varied from Table to Table. This is important because the data is not necessary comparable between tables, but trends are seen within each table.

In this regard, from Tables 6 and 7, it seems that, as level of CAPB increases, deposition drops. This is not true for all co-surfactants, however, since, as noted in Table 9, using amphoacetate, this trend was not seen.

For this reason, the level of CAPB in any surfactant system of our Invention should be less than 50%, preferably less than 40%, more preferably less than 30% of surfactant system.

Examples 10 and 11; N-acyl Derivatives of Taurine

In order to demonstrate effect, of N-acyl derivatives of taurine, applicants conducted the following test:

TABLE 10

| Formulation | Example 10 | Example 11 |
|---|---|---|
| Taurate |  | 3% |
| CAPB (cocoamidipropyl betaine) | 2.75% | 3% |
| Water | To balance | To balance |
| Glutamate (Sodium lauroyl glutamate) | 6.75% |  |
| Glycerin | 70% | 60% |
| Glycerin deposition (ug/cm$^2$) | 62.1 (+−1.9) | 46.3 (+−1.7) |

First, it is noted that Example 10 is identical to Example 3 at Table 5, except that it was done on different pigskin. If we scale up glycerin deposition from 62.1 μg/cm$^2$ (table above) to 99.24 μg/cm$^2$ to account for skin to skin variation, and taking into account that Example 11 only has 60% glycerin, the normalized glycerin deposition from taurate (Example 11) in comparison to examples in Table 5 will be 86.67 μg/cm$^2$. More specifically, it is well understood by those in the art that the mathematical normalization is as follows: if the same sample, with every procedure described being the same, pig A gives 99.24 ug/cm and pig B gives 62.1 ug/cm2 (these type of variation among pigs are quite common), there is a factor of 1.60 to scale up the number for pig B.

Further, applicants had previous data which showed that the amount of glycerin deposited is linearly proportional to the level of glycerin in a formulation up to 70% glycerin. Since example 11 in table 10 has 60% glycerin instead of 70%, there is another factor of 1.17 to scale up. Taking these two factors together, we obtain the figure of 86.67 for taurate noted (46.3 times 1.6 times 1.17). The reason we did not have a taurate formulation with 70% glycerin is because some of the formulation ingredients introduce water and there is not always enough "space" for 70% glycerin.

Thus, relative to the sulfate and CAPB system seen in Table 5 (Comparatives C and E), the taurate system is superior. It is also noted that, to compensate for different skin and the 1.17 factor difference in glycerin level in formulation, comparative C in table 5 (63.38 ug/cm2) will become 33.85 ug/cm2; and comparative E in table 5 (45.09) will become 24.09 ug/cm2. Both values are lower than example 11 at table 10 which is 46.3. Thus, these numbers are also consistent.

The invention claimed is:

1. A composition comprising:
   1) 55 to 90% by wt. glycerin;
   2) a surfactant system comprising:
      a) 3 to 12% by wt. of the total composition of a surfactant selected from the group consisting of salts of N-acyl derivatives of dicarboxylic amino acids, salts of N-acyl derivatives of monocarboxylic acids, salts of N-acyl derivatives of taurine, and mixtures thereof
      b) 1 to 15% by wt. of the total composition of a co-surfactant comprising a betaine and less than 50% by wt. of the surfactant system comprises the betaine; and
   3) 5 to 55% by wt. of the total composition of water.

2. The composition according to claim 1, wherein 50 to 90% by wt. of the surfactant system is the 2(a) surfactant.

3. The composition according to claim 1, wherein 60 to 80% by wt. of the composition comprises the glycerin.

4. The composition according to claim 1, wherein less than 40% of the surfactant system comprises the betaine.

5. The composition according to claim 1, wherein the betaine is alkyl amido betaine.

6. The composition according to claim 5, wherein less than 30% by wt. of the surfactant system comprises the alkyl amido betaine.

7. A method of enhancing glycerin deposition, the method comprising applying the composition of claim 1 to hair or skin.

8. The composition of claim 1, wherein the 2(a) surfactant comprises a salt of N-acyl glutamate.

9. The composition of claim 8, wherein the salt of N-acyl glutamate comprises sodium N-cocoyl-L glutamate, sodium N-lauroyl-L-glutamate, sodium N-myristoyl-L-glutamate, potassium N-cocoyl-I-glutamate, potassium N-lauroyl-L-glutamate, potassium N-myristoyl-Lglutamate, or a combination of two or more thereof.

10. The composition of claim 1, wherein the 2(a) surfactant comprises a salt of N-acyl taurate.

11. The composition of claim 1, wherein the betaine comprises cocoamidopropyl betaine.

12. The composition of claim 1, wherein the betaine comprises cocoamidopropyl betaine.

13. A composition comprising:
   1) 60 to 80% by wt. glycerin;
   2) a surfactant system comprising:
      a) 3 to 12% by wt. of the total composition of a surfactant selected from the group consisting of salts of N-acyl derivatives of dicarboxylic amino acids, salts of Nacyl derivatives of monocarboxylic acids, salts of N-acyl derivatives of taurine, and mixtures thereof;
      b) 1 to 10% by wt. of the total composition of a co-surfactant comprising cocoamidopropyl betaine; wherein 60 to 90% by wt. of the surfactant system comprises the 2(a) surfactant and less than 40% by wt. of the surfactant system comprises the cocoamidopropyl betaine; and
   3) 5 to 55% by wt. of the total composition of water.

14. The composition according to claim 13, wherein less than 30% by wt. of the surfactant system comprises the cocoamidopropyl betaine.

15. The composition according to claim 13, wherein the 2(a) surfactant comprises a salt of N-acyl glutamate.

16. The composition of claim 15, wherein the salt of N-acyl glutamate comprises sodium N-lauroyl-L-glutamate.

17. The composition of claim 1, wherein the composition has a conductance value of greater than 800 microseconds using a skin conductance test.

18. The composition of claim 1, wherein the composition has a transepidermal water loss value of less than 35 g/(m$^2$·h).

19. The composition of claim 1, wherein the composition has a deposition value of greater than 60 micrograms per square centimeter.

20. The composition of claim 13, wherein the composition has a deposition value of greater than 60 micrograms per square centimeter.

* * * * *